United States Patent [19]

Thakkar et al.

[11] Patent Number: 4,797,286

[45] Date of Patent: Jan. 10, 1989

[54] ORALLY ADMINISTERABLE SUSTAINED RELEASE PHARMACEUTICAL FORMULATIONS

[75] Inventors: Arvind L. Thakkar, Indianapolis; Lowell L. Gibson, Beech Grove, both of Ind.

[73] Assignee: Eli Lilly and Company, Indianapolis, Ind.

[21] Appl. No.: 797,305

[22] Filed: Nov. 12, 1985

[51] Int. Cl.$^4$ ............................................. A61K 9/64
[52] U.S. Cl. ..................................... 424/456; 424/457
[58] Field of Search ................. 514/200; 424/457, 456

[56] References Cited

U.S. PATENT DOCUMENTS 4,625,535 12/1986 Angerbauer et al. ............... 514/200

FOREIGN PATENT DOCUMENTS 1572226 7/1980 United Kingdom .
1590864 6/1981 United Kingdom .

OTHER PUBLICATIONS

Chemical Abstracts, vol. 89: 80177p "Effect of Hydrophilization of Hydrophobic on Release Rate from Capsules" Leck, C. F. et al J. Pharm. Sci. 1978, 67(7), 935–9.
Chemical Abstracts vol. 91, 1979: 27262c, "In vitro and In Viro Availability of Hydrophilized Phenytoin from Capsules", Lerk, C. F. et al., J. Pharm. Soi. 1979, 68(5), 634–8.
Hunter et al., Pharm. Ind. 45, 4, 433–434 (1983).
Product Bulletin, "The Hard Capsule with the Soft Centre", Elanco Products.
Product Bulletin, "Gelucire ®, Gattefosse Corporation (1983).
Francois et al., Pharm. Ind., 44, 1, 86–89 (1982).
Hunter et al., Pharm. Ind., 44, 1, 90–91 (1982).

Primary Examiner—Thurman K. Page
Assistant Examiner—L. R. Horne
Attorney, Agent, or Firm—Bruce J. Barclay; Leroy Whitaker

[57] ABSTRACT

This invention provides orally administerable pharmaceutical formulations having a semi-solid matrix containing a hydrophilic substance capable of creating channels in a hydrophobic carrier matrix thereby providing a sustained rate of release of an active agent from the formulation.

2 Claims, No Drawings

ORALLY ADMINISTERABLE SUSTAINED RELEASE PHARMACEUTICAL FORMULATIONS

BACKGROUND OF THE INVENTION

Gelatin capsules are widely used in the pharmaceutical industry for oral administration of a variety of active agents. In general, there are two types of gelatin capsules. Soft gelatin capsules are used to contain semisolids, liquids and pastes, and hard gelatin capsules are used to contain powders and granules. Soft gelatin capsules suffer from the disadvantages that they require significantly more gelatin for encapsulation of a given dose of pharmaceutically active compound than hard gelatin capsules, and that they are typically made and filled by contract manufacturers. Hard gelatin capsules are supplied by specialist manufacturers for filling by the producer of the material to be encapsulated. Quality control considerations favor capsule filling by the producer of the filling material and considerable increases in the price of gelatin favor the use of hard gelatin capsules. However, if hard gelatin capsules are used to contain materials other than powders and granules, there have been problems of leaking of capsule contents in handling. The leaking can only be overcome by time-consuming and cumbersome operations such as banding of the capsule after filling. Such operations add greatly to production costs.

Recently, a capsule filling medium which is semisolid, liquid or paste-like in nature has been developed which can be readily introduced into hard gelatin capsules without the expected problems of leakage. This thixotropic medium can be introduced into the capsule in a state of low viscosity and, once in the capsule, the medium assumes a relatively high viscosity, thereby reducing the tendancy of the medium to leak from the capsule. These formulations are described in detail in U.K. Pat. No. 1,590,864.

The use of semi-solid matrix formulations permits the control of the rate of release of the active agent in the formulation by altering the hydrophilic-lipophilic balance of the matrix. Matrices of high lipophilicity having a high melting point erode slowly, thereby delaying the release of the active agent from the matrix. In contrast, matrices that are highly hydrophilic and have melting points at or near about 37° C. will dissolve rapidly.

The present invention provides a sustained release pharmaceutical formulation in capsule unit dosage form comprising a gelatin capsule containing a semi-solid matrix comprising a pharmaceutically active agent, a pharmaceutically acceptable hydrophobic carrier matrix and a hydrophilic substance capable of providing diffusion channels into the hydrophobic carrier. The present formulation contains a non-dispersing, slow eroding hydrophobic matrix having a melting point greater than about 37° C. The hydrophobic nature of the matrix allows the formulation to retain its shape and physical integrity. In the absence of the hydrophilic additive the active agent is very slowly and incompletely released from the formulation. When the hydrophilic substance is incorporated into a formulation of the invention, water penetration into the formulation is promoted, thereby providing sustained release of the active agent. The hydrophilic additive absorbs water and causes the formulation to swell. Formulations of the invention containing a hydrophilic additive cause the active agent to be released more completely and over a more prolonged period of time.

SUMMARY OF THE INVENTION

The present invention provides a pharmaceutical formulation in capsule unit dosage form comprising a gelatin capsule containing a semi-solid matrix, said semi-solid matrix comprising a pharmaceutically active agent, a pharmaceutically acceptable hydrophobic carrier matrix and a hydrophilic substance capable of creating channels in the hydrophobic carrier matrix thereby providing a sustained rate of release of the active agent from the formulation.

DETAILED DESCRIPTION OF THE INVENTION

The concentrations described herein of the ingredients employed in a formulation of the invention are based only on the ingredients present in the semisolid matrix. Therefore, the total concentration of the semi-solid matrix constitutes 100% of the total formulation, as the weight of the capsules are not considered when calculating the percentages provided hereinafter.

The formulation of the present invention will contain a hydrophilic substance capable of creating channels in the hydrophobic carrier matrix thereby providing a sustained rate of release of the active agent from the formulation. The term "hydrophilic substance capable of creating channels in the hydrophobic carrier matrix", as defined herein, represents one or more substances which have an affinity for water and which tend to combine readily with water. Once this hydrophilic substance is incorporated in the present formulations the entry of water into the formulation is facilitated by creating diffusion channels into the hydrophobic carrier matrix so as to dissolve the pharmaceutically active agent and permit its release over a prolonged period of time.

The hydrophilic substance will be present in the formulation at a concentration in the range of about 10% to about 40% by weight, more preferably about 15% to about 30% by weight. Exemplary hydrophilic substances suitable for use herein include starch, microcrystalline cellulose, cellulose with sodium carboxymethylcellulose such as Avicel RC-591 (FMC Corporation), hydroxypropyl methylcellulose derivatives, such as Methocel K15M, from Dow Chemical Company, modified cellulose gums such as Ac-Di-Sol from FMC Corporation and natural mucilagenous substances such as powdered psyllium.

Any number of pharmaceutically active agents may be employed in the formulations of the present invention. These active agents may exist as either solids or liquids at standard temperature and pressure. Exemplary pharmaceutically active agents suitable for use herein include, but are not limited to, the cardiovascular drugs such as propranolol; the central nervous system compounds such as haloperidol; the non-steroidal anti-inflammatory agents such as piroxicam, indomethacin, fenoprofen and ibuprofen; the antidepressants such as fluoxetine and tomoxetine; and the antibacterial agents such as cefaclor, amoxicillin, ampicillin and especially cephalexin. Other pharmaceutically active agents capable of oral administration may also be used herein. The quantity of active agent present in a formulation of the invention will be from about 0.1% to about 60% by weight, more preferably from about 15% to about 40% by weight.

A variety of pharmaceutically acceptable hydrophobic carrier matrices may be employed in the formulation of the invention. The quantity of hydrophobic carrier matrix present in a formulation of the invention will be in the range of about 30% to about 60% by weight, more preferably about 40% to about 55% by weight. The hydrophobic carrier matrices employed herein are amphiphiles in which the molecule or ion contains both hydrophilic and lipophilic portions. These matrices can be defined by a numerical value based on the Hydrophile-Lipophile Balance system, called the HLB system. The HLB scale is a numerical scale, extending from 0 to approximately 50, where lower numbers denote more lipophilic and hydrophobic substances, and higher numbers denote more hydrophilic and lipophobic substances. The affinity of a compound for water, or for oily substances, is determined and its HLB value is assigned experimentally. Tables of such values have been published and formulation chemists are aware of them. The HLB of the hydrophobic carrier matrix employed in the present formulation will be in the range of about 1 to about 10. Suitable pharmaceutically acceptable hydrophobic carriers include the glycerides and partial glycerides. The preferred carriers are known under the trademark Gelucire, and are commercially available from Gattefosse Corporation, Hawthorne, N.Y. Gelucires are available with varying physical characteristics such as melting point, HLB and solubilities in various solvents. The preferred Gelucire is Gelucire 46/07, a substance commonly employed in hard gelatin capsules.

The formulations of the present invention are prepared by procedures well known to one of ordinary skill in the art. Typically, the pharmaceutically acceptable hydrophobic carrier matrix is melted, if necessary, to provide a flowable liquid thereby making it easier to obtain a homogeneous mixture. The active agent and hydrophilic substance are next added to the liquid carrier, and the ingredients are combined to provide a homogeneous mixture of the semi-solid matrix.

The semi-solid matrix is placed in capsules prior to administration to the patient in need of treatment. Such capsules may be hard or soft, although semi-solid matrix technology is more routinely associated with hard capsules. The semi-solid matrix employed in the present formulation may be filled into hard gelatin capsules using standard capsule filling machinery modified in that the conventional powder filling parts are replaced with a semi-solid filling head. These filling heads are known and readily available from a variety of commercial vendors.

The formulations of the present invention are believed to provide prolonged gastric retention by one or both of the following mechanisms. The formulations are composed of a hydrophilic substance which causes swelling of the hydrophobic carrier matrix, thereby prolonging the formulation's gastric residence and delaying the passage of the formulation past the pylorus into the intestinal tract. As such, the active agent is released over a prolonged period of time. The present formulation may also have bioadhesive properties, such that the formulation actually interacts with the mucous layer of the stomach. However, regardless of their mechanism of action, the present formulations are not limited by any mode of operation.

The following Examples illustrate specific formulations comprehended by the present invention, and methods for their preparation. The Examples are not intended to be limiting to the scope of the invention in any respect and should not be so construed.

EXAMPLE 1

To 7.5 g (41.7% by weight) of molten Gelucire 46/07 heated on a 70° C. water bath was added 6.0 g (33.3% by weight) of cephalexin monohydrate, 4.5 g (25% by weight) of Avicel RC-591. The mixture was stirred and added to clear 000 hard gelatin capsules to provide filled capsules weighing approximately 1.5 g each.

EXAMPLE 2

To 9.0 g (50% by weight) of molten Gelucire 46/07 at 70° C. was added 6.0 g (33.3% by weight) of cephalexin monohydrate and 3.0 g (16.7% by weight) of powdered psyllium seed containing 85% husks (40 mesh). The mixture was stirred until homogeneous and placed into size 000 hard gelatin capsules, each weighing 1.6 g following filling with the mixture.

EXAMPLE 3

A mixture of 9.0 g (50.0% by weight) of molten Gelucire 46/07, 6.0 g (33.3% by weight) of cephalexin monohydrate and 3.0 g (16.7% by weight) of Methocel K15M was added to 000 hard gelatin capsules.

EXAMPLE 4

To 5.0 g (50% by weight) of molten Gelucire 46/07 at 70° C. was added 3.0 g (30% by weight) of Avicel RC-591 and 2.0 g (20% by weight) of (−)-N-methyl-3-(2-methylphenoxy)-3-phenylpropylamine hydrochloride (tomoxetine hydrochloride). The resulting mixture was stirred until homogeneous. The mixture was placed into size 0 capsules. The final capsules weighed approximately 300 mg each.

EXAMPLE 5

To 3.375 g (50% by weight) of molten Gelucire 46/07 under agitation was added 2.025 g (30% by weight) of Avicel RC-591 and 1.35 g (20% by weight) of tomoxetine hydrochloride. The mixture was stirred until homogeneous. The mixture was placed into size 0 clear capsules, each filled capsule weighing about 225 mg, and an additional 15 mg of tomoxetine hydrochloride was added to each capsule.

The following procedure was used to determine the level of cephalexin in the plasma of dogs following administration of a formulation of the invention. Six fed dogs were orally administered one capsule each of the specified formulation of the invention. Blood samples were taken from the dogs at about 0, 0.5, 1.0, 1.5, 2.0, 3.0, 4.0, 6.0, 8.0, 10.0, 12.0, 14.0 and 24.0 hours after administration. The blood samples were centrifuged and the plasma samples were frozen during storage. The frozen plasma samples were warmed to room temperature and 0.5 ml of plasma was added to a microcentrifuge tube. To the plasma was added 0.5 ml of 10% aqueous trichloroacetic acid (v/v) and the resulting mixture was centrifuged for seven minutes. The supernatant was chromatographed over an HPLC silica gel column and compared to a reference standard.

A reference standard was prepared from plasma obtained from blood samples drawn from dogs just prior to administration with a formulation of the invention. This standard was prepared by adding 0.125 ml of an aqueous solution of cephalexin monohydrate and 0.125 ml of 20% aqueous trichloroacetic acid (v/v) to 0.25 ml of plasma in a microcentrifuge tube. The resulting mixture was centrifuged for seven minutes and the supernatant was chromatographed on an HPLC column. The results of this test are set forth below in Table I as the average of n trials.

TABLE I

Plasma Levels of Cephalexin in Dogs (μg/ml)

| Time After Administration (hours) | Example No. | | |
|---|---|---|---|
| | 1 (n = 3) | 2 (n = 6) | 3 (n = 3) |
| 0 | 0 | 0 | 0 |
| 0.5 | 0 | 0.22 | 0 |
| 1.0 | 0 | 1.52 | 0 |
| 1.5 | 0.24 | 2.80 | 0.71 |
| 2.0 | 0.75 | 4.06 | 2.04 |
| 3.0 | 2.88 | 6.98 | 4.54 |
| 4.0 | 6.40 | 9.00 | 7.19 |
| 6.0 | 12.60 | 11.67 | 9.02 |
| 8.0 | 15.88 | 11.00 | 8.35 |
| 10.0 | 15.40 | 10.02 | 8.22 |
| 12.0 | 11.33 | 8.60 | 7.39 |
| 14.0 | 8.16 | 7.98 | 6.05 |
| 24.0 | 1.67 | 3.50 | 0.58 |

A similar study was carried out with the formulation of Example 4 described above. This study measured the plasma level of tomoxetine hydrochloride in dogs at various times following oral administration of the formulation. Each of three dogs was dosed with 60 mg of the active agent and an average was obtained. The results of this study are set forth below in Table II.

TABLE II

Plasma Levels of Tomoxetine Hydrochloride

| Time After Administration (minutes) | Plasma Level of Active Agent in Dogs (μg/ml) |
|---|---|
| 30 | 0 |
| 60 | 0.05 |
| 90 | 0.10 |
| 120 | 0.14 |
| 180 | 0.41 |
| 240 | 0.56 |
| 360 | 0.80 |
| 480 | 0.56 |
| 600 | 0.37 |
| 720 | 0.20 |
| 840 | 0.12 |
| 1440 | 0.02 |

We claim:

1. A pharmaceutical formulation in capsule unit dosage form comprising a gelatin capsule containing a semi-solid matrix, said semi-solid matrix comprising an antibacterial agent, a pharmaceutically acceptable hydrophobic carrier matrix and a hydrophilic substance capable of creating channels in the hydrophobic carrier matrix thereby providing a sustained rate of release of the active agent from the formulation.

2. The formulation of claim 1 wherein the antibacterial agent is cephalexin.

* * * * *